United States Patent
Sakamoto

(10) Patent No.: US 7,198,782 B2
(45) Date of Patent: Apr. 3, 2007

(54) METHOD FOR THE TREATMENT OF DIABETES

(76) Inventor: Kenji Sakamoto, 25. Aza Kourokuzawa, Memeki, Yuuwa-machi, Kawahe-gun, Akita 010-1233 (JP)

( * ) Notice: Subject to any disclaimer, the term of this patent is extended or adjusted under 35 U.S.C. 154(b) by 465 days.

(21) Appl. No.: 10/397,507

(22) Filed: Mar. 26, 2003

(65) Prior Publication Data

US 2004/0229223 A1 Nov. 18, 2004

Related U.S. Application Data

(62) Division of application No. 09/924,890, filed on Aug. 8, 2001, now Pat. No. 6,608,173, which is a division of application No. 09/647,705, filed on Nov. 7, 2000, now abandoned.

(30) Foreign Application Priority Data

Apr. 4, 1998 (JP) ................................. 10-108662
Apr. 8, 1998 (JP) ................................. 10-112819

(51) Int. Cl.
*A61K 46/42* (2006.01)
*A61K 38/04* (2006.01)
*A61K 38/08* (2006.01)

(52) U.S. Cl. ..................................... 424/93.1; 530/326

(58) Field of Classification Search ................ 530/300, 530/303, 328; 424/93.1
See application file for complete search history.

(56) References Cited

OTHER PUBLICATIONS

Lazar et al. Molecular and Cellular Biology 1988, vol. 8, No. 3, pp. 1247-1252.*
Amanda et al. J. Biol. Chemis. 1999, vol. 274, No. 45, pp. 32478-32485.*
Song I et al. The human gastrin/cholecystokinin type B receptor gene: Alternative splice donor site in exon 4 generates two variant MRNAs. Proc.natl.Acad.Sci.USA., 90: 9085-9089, 1993.
Naranda T et al. A peptide derived from an extracellular domain selectively inhibits receptor internalization: target sequences on insulin and insulin-like growth factor I receptors. Proc.Natl.Acad. Sci.USA., 94: 11692-11697, 1997.

* cited by examiner

*Primary Examiner*—Bruce R. Campell
*Assistant Examiner*—Bao Qun Li
(74) *Attorney, Agent, or Firm*—Brooks Kushman PC

(57) ABSTRACT

A method for efficiently searching novel physiologically active substances under a certain predictability. This searching method comprises, among receptors of cells producing an antagonist to a substance in vivo or receptors of cells producing an antagonist to the cells per se, finding a receptor having amino acid sequences of two or more sizes by comparing the cDNA sequences of the receptor, and then examining which region in the longer receptor is missed in the shorter receptor by comparing the above cDNA sequences. By using this method, remedies for diabetes comprising a peptide having the amino acid sequence represented by SEQ ID NO:1 or 5, insulin production regulators comprising a peptide having the amino acid sequence represented by SEQ ID NO:2, and gastric secretion inhibitors comprising a peptide having the amino acid sequence represented by SEQ ID NO:3 or 4 are provided.

8 Claims, No Drawings

SEQUENCE LISTING

<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Artificial polypeptide which inhibits insulin
      production.

<400> SEQUENCE: 1

Pro Lys Ala Pro Ser Ala Gln
1               5

```
<210> SEQ ID NO 2
<211> LENGTH: 28
<212> TYPE: PRT
<213> ORGANISM: Artificial Sequence
<220> FEATURE:
<223> OTHER INFORMATION: Artificial peptide which regulates insulin
      production

<400> SEQUENCE: 2

Val Gly Arg Asp Pro Ala Ala Pro Ala Leu Trp Arg Arg Arg Gly
1               5                   10                  15

Thr Ala Pro Pro Leu Ser Ala Ile Val Ser Gln Val
            20                  25

<210> SEQ ID NO 3
<211> LENGTH: 5
<212> TYPE: PRT
<213> ORGANISM: Artificial Sequence
<220> FEATURE:
<223> OTHER INFORMATION: Artificial polypeptide which regulates insulin
      production.

<400> SEQUENCE: 3

Gly Gly Ala Gly Pro
1               5

<210> SEQ ID NO 4
<211> LENGTH: 11
<212> TYPE: PRT
<213> ORGANISM: Artificial Sequence
<220> FEATURE:
<223> OTHER INFORMATION: Artificial polypeptide having inhibitory effect
      on gastric
      acid secretion

<400> SEQUENCE: 4

Met Ser Val Gly Gly Asn Met Leu Ile Ile Val
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Artificial polypeptide having inhibitory
      effects on insulin
      secretion

<400> SEQUENCE: 5

Pro Gln Val Pro Ser Ala Gln
1               5

<210> SEQ ID NO 6
<211> LENGTH: 12
<212> TYPE: PRT
<213> ORGANISM: Artificial Sequence
<220> FEATURE:
<223> OTHER INFORMATION: Artificial polypeptide which promotes
      growth hormone
      secretion.

<400> SEQUENCE: 6

Pro Ser Cys Gln Trp Val Gln Ala Pro Ala Cys Gln
1               5                   10
```

METHOD FOR THE TREATMENT OF DIABETES

CROSS-REFERENCE TO RELATED APPLICATIONS

This application is a divisional of U.S. application Ser. No. 09/924,890, filed on Aug. 8, 2001, now U.S. Pat. No. 6,608,173 which is a divisional of U.S. application Ser. No. 09/647,705 filed on Nov. 7, 2000 now abandoned.

TECHNICAL FIELD

The invention relates to a method for searching various types of novel physiologically active substances and a process for producing same, and drugs found by the searching method.

RELATED ART

In the prior art, the searching for unknown physiologically active substances involved analyzing constituents present in body fluids or tissues, identifying and isolating novel substances and investigating the physiological activity of the discovered novel substances.

The method of the prior art described above consists of analyzing constituents present in the body, finding novel substances and investigating their physiological activities. However, the number of constituents present in the body is extremely high, and physiologically active substances are often present only in low concentrations, thereby making finding novel substances a difficult task. Further, because an overwhelming number of physiological reactions take place in the body, and thus, finding the nature of physiological activities the newly found substances have is also difficult. Therefore, finding novel physiologically active substances with the method of the prior art is a difficult task.

DISCLOSURE OF THE INVENTION

Therefore, one of the objects of the invention is to provide a more efficient method for searching novel physiologically active substances with a certain level of predictability. Furthermore, another one of the objects of the invention is to provide a process for producing the physiologically active substances found by the method described above. In addition, one of the objects of the invention is to provide a novel medicine for treating diabetes, insulin production regulators, gastric acid secretion regulators and growth hormone secretion regulators found by the method of the invention described above.

The inventors have previously invented a more efficient method for searching novel physiologically active substances with a certain level of predictability and filed a patent application (Patent Laid-open Publication No Hei. 10-109997). The method is based on the finding that, among receptors of substances, for which substances or cells having antagonizing effects are present in a body, or, receptors for the Substance A, for which cells or substances having antagonizing effects on cells responding to said Substance A are present in a body, when there exist two or more sizes for the same receptor, the missing portions, i.e. the portions of amino acid sequences which have been spliced, have physiological activities related to said receptor.

The inventors completed the invention after actually verifying that, in performing the searching method of the previously applied patent described above, the method of inferring the amino acid sequences of receptors based on the base sequences of their cDNAs is also valid when two or more cDNA sequences exist for said receptors, and that its is not restricted to the ones based on the amino acid sequences of receptors whose actual existences are known.

Namely, the invention provides a method for searching physiologically active substances comprising, examining a peptide having an amino acid sequence of two or more sizes for the same receptor by comparing the cDNA sequences of said receptor, wherein the receptor is a receptor of a cell producing an antagonist to a substance present in a body or a receptor of a cell producing an antagonist to said cells per se, and then examining which regions of the longer receptor are missing in the shorter receptor by comparing the sequences of the above-mentioned cDNAs. Also, the invention provides a method for producing physiologically active peptides wherein the missing regions, established by the method of the invention described above, or their derivatives are produced. In addition, the invention provides a medicine for treating diabetes comprising, as an active component, a peptide having the effect of increasing the production of insulin by insulin producing cells, said peptide being those successfully searched for and found by the method of the invention described above and having the amino acid sequences indicated by the sequence numbers 1 or 5 of the sequence table, or having amino acid sequences obtained by the substitution inside, deletion from, insertion into or addition to said sequence (number 1 or 5) of one or several amino acids. In addition, the invention provides insulin production regulators comprising, as an active component, a peptide having the effect of regulating the production of insulin by insulin producing cells, said peptides having the amino acid sequence indicated by the sequence number 2 of the sequence table, or having amino acid sequences obtained by the substitution inside, deletion from, insertion into or addition to said sequence (number 2) of one or several amino acids. In addition, the invention provides gastric acid secretion regulators comprising, as an active component, a peptide having the effect of regulating the secretion of gastric acid, said peptides having the amino acid sequences indicated by the sequence numbers 3 or 4 of the sequence table, or having amino acid sequences obtained by the substitution inside, deletion from, insertion into or addition to said sequence (numbers 3 or 4 ) of one or several amino acids. Growth hormone production regulators are provided, comprising, as an active component, peptides having the effects of regulating the production of hormone, and having the amino acid sequence indicated by the sequence number 6 of the sequence table or having amino acid sequences obtained by the substitution inside, deletion from, insertion into or addition to said sequence (number 6) of one or several amino acids.

The invention provides a method based on the base sequences of cDNAs, for efficiently searching novel physiologically active substances with a certain level of predictability. In the method of the invention, novel biologically active substances can be found by examining the receptors for substances participating in antagonism, therefore, it is not required as in the prior art, to isolate physiologically active substances present in trace amounts inside biological samples containing extremely large number of constituents. In addition, the physiological activity of the searched and found physiologically active substance is an activity participating in the antagonism described above, therefore, searching for its physiological activity is also considerably easier than that of the prior art. Thus, according to the method of the invention, searching for novel physiologically active substances can be performed with a considerably higher efficiency compared to the related art. Also, the invention provides a novel medicine for treating diabetes having excellent increased effects on insulin production. In addition, novel insulin production regulators, gastric acid secretion regulators and growth hormone production stimulators are provided.

PREFERRED EMBODIMENTS OF THE INVENTION

In the method for searching physiologically active substances of the invention, among receptors of cells producing an antagonist to a substance in a body, or among receptors of cells producing an antagonist to said cells per se, amino acid sequences of two or more sizes for a same receptor are examined by comparing the cDNA sequences of the receptor and then which region of the longer receptor is missing in the shorter receptor is examined by comparing the sequences of the above-mentioned cDNAs or the sequences of mature mRNAs.

Namely, the method of the invention concerns cases where two or more receptors with different sizes are generated based on the differences in the base sequences of the mature mRNAs. In other words, the method of the invention searches for splicing variations at the level of the mRNAs. The role of splicing resulting from the splicing variation at the level of mRNAs, which normally does not occur, is not well understood, except that it inactivates gene expression. There are cases where sequences which should originally be translated are consequently not translated, and in contrast, there are cases where sequences which should not be translated are expressed. In most instances, because splicing is not properly performed, even amino acids can not be expressed, but in the other instances, there are actual cases where amino acid sequences generated by splicing or those which are to be deleted function effectively. The method of the invention consists of searching for such splicing variations at the level of mRNAs.

The method of the invention is directed to examining the base sequences of the cDNAs for the above-mentioned receptors and finding those for which cDNAs of the same receptor exist in different sizes. This task can be performed by either determining several times the base sequences and the sizes of the cDNAs for said receptors or, if the information is reported in the literature, by using this information. The glucagon receptor, FGF receptor and GIP receptors can be mentioned as examples of receptors for which two or more cDNAs of the same receptor exist in different sizes.

The physiologically active substances can be obtained by producing peptides identical to the missing sequence regions which have been recognized to contain physiological activity. In most cases, the missing regions consist of relatively short peptides, such that said physiologically active substances may be produced easily by chemical synthesis using commercially available peptide synthesizers, in such cases. Or, it is possible to produce them using genetic engineering techniques of the art.

The physiological activity of the physiologically active substances obtained participate in the antagonism mentioned above and can therefore be easily verified by suitable methods satisfying the respective antagonistic effects.

In addition, it is well known by those skilled in the art that among peptides having physiological activity in general, there are cases where the physiological activity is maintained even when a small number of amino acids are substituted with other amino acids, a small number of amino acids are added, or a small number of amino acids are deleted. Therefore, also in the scope of the invention is the production of substances having the physiological activities of the physiologically active substances consisting of the missing regions mentioned above, having a small number of amino acids substituted by other amino acids, a small number of amino acids added, or a small number of amino acids deleted, among the amino acids constituting the missing regions mentioned above (in the present application of the invention, such substances are called "derivatives" of the missing regions mentioned above). Preferably, such derivatives have more than 70%, even more preferably 90% homology with the missing regions mentioned above.

The inventors found a peptide having the effect of increased production of insulin by insulin producing cells, using the search method of the invention described above. Since this peptide has the effect of increased production of insulin by insulin producing cells, it is effective as a medicine for treating diabetes, i.e., as mentioned in the embodiments described below, the existence of several types of cDNAs with different sizes for the glucagon receptors is mentioned in literature in the public domain, and by comparing the base sequences of these cDNAs, which regions of the base sequence coding for the longer amino acid sequence are missing from the base sequence coding for the shorter amino acid sequence was examined, and the amino acid sequence of the missing region was inferred (sequence number 1). Then, the peptide having the amino acid sequence indicated by the sequence number 1 was chemically synthesized and when administered to insulin producing cells, the production of insulin by said cells increased significantly. This led to the knowledge that the peptide having the amino acid sequence indicated by the sequence number 1 is effective as a remedy for diabetes.

In addition, peptides having the amino acid sequence of the sequence number 1 in which one or several amino acids have been substituted, deleted, inserted or added, and having the effect of increasing the production of insulin by insulin producing cells, are also in the scope of the invention. An actual example of such peptides is the peptide having the amino acid sequence represented by the sequence number 5, which was found based on the method of the invention, by comparing the cDNAs for the rat glucagon receptor. In addition, peptides having the effect of increasing the production of insulin, other than the peptides with amino acid sequences represented by the sequence number 1 or 5, should preferably have more than 70%, even more preferably 90% homology with the sequences indicated by the sequence number 1 or 5. Also, while the number of amino acids is not specifically restricted for these peptides, from the perspective of ease of synthesis and antigenicity, about 7 to 20 is preferable, about 7 to 10 is even more preferable. Non-oral administrations such as intravenous injection, intra-muscular injection or enteral administration are preferred for the administration route of the remedy for diabetes of the invention mentioned above. Also, while the dose is suitably determined based on the condition of the patient and the molecular weight of the active principle, 0.01 to 1.0 mg per day for 1 kg body weight is normally preferred. Further, the remedy can be produced suitably by the methods of the art, and can be used dissolved in physiological saline solutions with a concentration range of 30 to 3000 mg/l, for instance.

In addition, similarly to above, the inventors found a peptide regulating the production of insulin (inhibition or stimulation of production). Its amino acid sequence is indicated by the sequence number 2. This sequence was found based on the search method of the invention described above, by comparing the cDNA sequences of the Glucose-dependent insuilinotropic polypeptide receptor. When stimulating the production of insulin, similarly to the above, it is effective as a remedy for diabetes. When inhibiting the production of insulin, it is effective as a remedy for hypoglycemia. Peptides effective as insulin production regulators are not restricted to peptides having the amino acid sequence indicated by the sequence number 2, and peptides having the amino acid sequence of the sequence number 2 in which one or several amino acids have been substituted, deleted, inserted or added, and having the effect of regulating the production of insulin by insulin producing cells, are also in the scope of the invention. In such cases, these peptides should preferably have more than 70%, even more preferably 90% homology with the sequences indicated by the sequence number 2. Also, while the number of amino acids is not specifically restricted for these peptides, from the perspective of ease of synthesis and antigenicity, about 25 to 50 is preferable, and about 28 to 35 is even more preferable.

Non-oral administrations such as intravenous injection, intra-muscular injection or enteral administration are preferred for the administration route of the insulin production regulator of the invention mentioned above. Also, while the dose is suitably determined based on the condition of the patient and the molecular weight of the active principle, 0.01 to 1.0 mg per day for 1 kg body weight is normally preferred.

Also, the remedy can be produced suitably by the methods of the art, and can be used dissolved in physiological saline solutions with a concentration range of 30 to 3000 mg/l, for instance.

Furthermore, similarly to above, the inventors found peptides regulating the secretion of gastric acid (inhibition of secretion or stimulation of secretion). Their amino acid sequences are indicated by the sequence numbers 3 and 4. These sequences were found based on the search method of the invention described above, by comparing the cDNA sequences of the gastrin receptor. These peptides, because they regulate the secretion of gastric acid, are effective as remedies for gastric and duodenal ulcers (in the case of secretion inhibition), or as remedies for the conditions of unsufficient gastric acid secretion (in the case of secretion stimulation). Peptides effective as gastric acid secretion regulators are not restricted to peptides having amino acid sequences indicated by the sequence number 3 or 4, and peptides having the amino acid sequence of the sequence number 3 or 4 in which one or several amino acids have been substituted, deleted, inserted or added, and having the effect of regulating the secretion of gastric acid, are also in the scope of the invention. In such cases, these peptides should preferably have more than 70%, even more preferably 90% homology with the sequences indicated by the sequence number 3 or 4. Also, while the number of amino acids is not specifically restricted for these peptides, from the perspective of ease of synthesis and antigenicity, in the case of sequences indicated by the sequence number 3, about 5 to 20 is preferable, about 5 to 8 is even more preferable, and in the case of sequences indicated by the sequence number 4, about 11 to 30 is preferable, and about 11 to 20 is even more preferable.

Non-oral administrations such as intravenous injection, intramuscular injection or enteral administration are preferred for the administration route of the gastric acid secretion regulators of the invention mentioned above. Also, while the dose is suitably determined based on the condition of the patient and the molecular weight of the active principle, 0.01 to 1.0 mg per day for 1 kg body weight is normally preferred. Also, the remedy can be produced suitably by the methods of the art, and can be used dissolved in physiological saline solutions with a concentration range of 30 to 3000 mg/l, for instance.

Furthermore, the inventors found a peptide regulating the production of growth hormones (stimulation of production or inhibition of production). Its amino acid sequence is indicated by the sequence number 6. This peptide, because it can regulate the production of growth hormones, is effective as remedies for dwarfism (in the case of stimulation of production), or as remedies for gigantism (in the case of inhibition of production). Peptides effective as growth hormone production regulators are not restricted to peptides having the amino acid sequence indicated by the sequence number 6, and peptides having the amino acid sequence of the sequence number 6 in which one or several amino acids have been substituted, deleted, inserted or added, and having the effect of stimulating the secretion of growth hormones, are also in the scope of the invention. In this case, these peptides should preferably have more than 70%, even more preferably 90% homology with the sequences indicated by the sequence number 6. Also, while the number of amino acids is not specifically restricted for these peptides, from the perspective of ease of synthesis and antigenicity, in the case of sequences indicated by the sequence number 6, about 12 to 30 is preferable, and about 12 to 20 is even more preferable.

Non-oral administrations such as intravenous injection, intramuscular injection or enteral administration are preferred for the administration route of the growth hormone production regulators of the invention mentioned above. Also, while the dose is suitably determined based on the condition of the patient and the molecular weight of the active principle, 0.01 to 1.0 mg per day for 1 kg body weight is normally preferred. Also, the remedy can be produced suitably by the methods of the art, and can be used dissolved in physiological saline solutions with a concentration range of 30 to 3000 mg/l, for instance.

EXAMPLES

In the following examples, the invention will be actually explained. It should be evident that the invention is not limited by these examples.

Example 1

Prediction of the Physiologically Active Peptide from the Glucagon Receptor

The amino acid sequence of the rat glucagon receptor described in FEBS Letters 351 (1994) 271–275 has been investigated. The glucagon receptor has four cDNA lengths reported from the base sequences of the cDNAs, and it is clear that two among them can be translated into amino acids. These are the consequences of a difference in the post-transcriptional splicing, and differ in their mode from the post-translational splicing such as in the case of the calcitonin receptor. However, the inventors predicted that the portion of amino acids generated by the difference in post-translational splicing also have some sort of activity. This amino acid sequence is indicated by the sequence number 1 of the sequence table.

Example 2

Production of the Peptide

A commercially available peptide synthesizer was used to synthesize the peptide having the amino acid sequence indicated by the sequence number 2.

Example 3

Stimulating Effect on Insulin Secretion

BxPC-3 cells which are insulin producing cells derived from a human pancreas (source: Dainippon Pharmaceutical Co.,Ltd. ), were cultured in RPMI 1640 media containing 10% calf fetal serum, and grown with 5% carbon dioxide gas in a humidified incubator at 37° C. The cells were treated with trypsin prior to seeding with a density of $1\times10^5$/well; when they reached confluency, the peptide of the invention synthesized in Example 2, the peptides A and B, which are unrelated to the invention and whose activities are unknown, as well as a control (physiological saline) were added at 0.01 mg/well, and the cells were cultured for 24 hours. Then, the concentrations of insulin present in the supernatents were measured by colorimetry with an insulin assaying kit (source: Shibayagi Co.,Ltd.). The results are presented in the Table 1, below.

TABLE 1

| samples | insulin concentration (µg/ml) |
|---|---|
| peptide of the invention | 148 |
| control | 37.6 |
| peptide A | 34.8 |
| peptide B | 87.1 |

As clearly demonstrated in Table 1, the peptide mentioned above, which has been searched for and found with the method of the invention, promotes the production of insulin by the insulin producing BxPC-3 cells. Therefore, the peptide is considered to work effectively for diabetes patients through its insulin synthesizing action.

Example 4

Production of the Peptides

A commercially available peptide synthesizer was used to synthesize the peptides having the amino acid sequences indicated by the sequence numbers 1 and 5 which were predicted based on the cDNA sequences of the human glucagon receptor.

Example 5

Stimulating Effect on the Production of Insulin by Insulin Producing Cells

HIT cells, which are insulin producing hamster pancreatic cells, and BxPC-3 cells, which are human pancreatic cells (source: Dai Nippon Seiyaku), were cultured in RPMI 1640 media (source: Dai Nippon Seiyaku) containing 10% calf fetal serum, and grown with 5% carbon dioxide gas in a humidified incubator at 37° C. The cells were treated with trypsin for seeding 96-well culture plates with a density of $1\times10^4$/well; when the cells reached confluency, the media was exchanged to a F12 serum-free media and the cells were cultured for 8 hours. Then, the peptides of the invention produced in Example 4 were dissolved in serum-free RPMI 1640 media; various doses of the peptides indicated by the sequence number 1 for the HIT cells, and various doses of the peptides indicated by the sequence number 5 for the BxPC-3 cells, were added to the wells and the cultures were further maintained for 12 hours. After the cultures have been performed, the stimulatory effects of the peptides of the invention on the production of insulin by the cells were measured by the insulin immunoassay, to seek stimulatory effects on production in comparison to the non-treated groups. Also, the insulin immunoassay, and the calculations for the rates of stimulation for the production of insulin were actually performed as follows. Various dilutions of the supernatents from the cell culture media were added to the wells coated with immobilized anti-insulin antibodies, and reacted with anti-insulin antibody solutions, according to the protocol of the insulin assay kit commercialized by Shibayagi (Ltd.). The detection was by reacting the biotin labeling the antibodies with the steptavidin-conjugated peroxydase and measuring the coloration catalyzed by the peroxydase. The concentration of insulin was calculated from a standard curve for insulin. When examining the rates of stimulation for the production of insulin in the groups with various doses added, by taking the rate of stimulation for the production of insulin in the reference group with no substance added as 100%, the following was obtained. The results are presented in the Table 2 below.

TABLE 2

| quantity of peptide added (µg/well) | rate of stimulation for the production of insulin (%) | |
|---|---|---|
| | HIT cells | BxPC-3 cells |
| 0 | 100.0 | 100.0 |
| 0.01 | 102.8 | 110.9 |
| 0.1 | 131.6 | 123.3 |
| 1 | 184.9 | 198.2 |
| 10 | 203.1 | 181.1 |

As clearly demonstrated in Table 2, the peptides mentioned above, which have been searched for and found with the method of the invention, have the effect on the insulin producing cells derived from hamster and human, of stimulating the production of insulin. Therefore, the peptides are considered as leading to a decrease in the level of blood sugar and thereby are useful for the treatment of diabetes.

Example 6

Production of Peptides

A commercially available peptide synthesizer was used to synthesize the peptides having the amino acid sequences indicated by the sequence numbers 3 and 4 which were predicted by comparing the cDNA sequences of the gastrin receptor.

Example 7

Inhibitory Effect on the Secretion of Gastric Acid in Rats

The inhibitory effect on the secretion of gastric acid was evaluated using rats (Wister line), by dissolving in physiological saline, the peptides synthesized in Example 6 and gastrin, a stimulator of gastric acid secretion, hypodermically injecting the previous solution, and measuring the secretion of gastric acid 10 minutes later. Gastrin was administered to obtain a dose of 4 µg/kg and the peptides of the invention were administered to obtain a dose of 10 µg/kg. The rats were immobilized on a fixator, their gastric juice was sampled by inserting a probe through the mouth into the stomach, and the pH was measured to evaluate the secretion of gastric acid. When the secretion of gastric acid was compared between the reference group with no substance administered and the administered group, the following was obtained for the inhibition on the secretion of gastric acid. The results are presented in the Table 3 below.

TABLE 3

| | Secretion of gastric acid (pH) | |
| --- | --- | --- |
| | Sequence No. 3 | Sequence No. 4 |
| Control | 3.2 | 3.1 |
| administered group | 5.3 | 4.8 |

As clearly demonstrated in Table 3, the peptides mentioned above, which have been searched for and found with the method of the invention, have the effect of inhibiting the secretion of gastric acid in rats. Therefore, the peptides are useful a gastric and duodenal ulcer remedies which inhibit secretion of gastric acid.

Example 8

Production of the Peptide

A peptide having the amino acid sequence indicated by the sequence number 6, which was predicted by comparing the amino acid sequences of somatostatin receptor, was synthesized with a commercially available peptide synthesizer.

Example 9

Stimulation of the Production of Growth Hormone by Growth Hormone Producing Cells Hamster-derived GH3 cells (source: IFO, deposition No. 50105), which are growth hormone-producing hypophyseal cells, were grown in an F12 media (source: Dai Nippon Seiyaku) containing 15% calf fetal serum, and grown with 5% carbon dioxide gas in a humidified incubator at 37° C. The cells were treated with trypsin for seeding 96-well culture plates with a density of $1 \times 10^4$/well; when the cells reached confluency, the media was exchanged to a 15% serum F12 media and the cells were cultured for 12 hours. Then, the peptides of the invention produced in Example 7 were dissolved in 15% serum F12 media to add various doses of the peptides to the wells, and the cultures were further maintained for 3 days. After the cultures have been performed, the stimulatory effects of the peptides on the production of growth hormones by the cells were measured by the growth hormone immunoassay, to examine stimulatory the effects on the production, in comparison with the non-treated groups. Also, the growth hormone immunoassay was performed with a method of the art, the sandwich ELISA, i.e., various dilutions of the supernatents from the cell culture media were added to wells coated with immobilized anti-growth hormone antibodies, and reacted for 180 minutes at room temperature, washed before further addition of anti-growth hormone antibodies labeled with peroxydase, and reacted for 60 minutes at room temperature. After washing, the coloring reaction catalyzed by the peroxydase was measured by measuring the absorbance. The concentration of growth hormone was examined based on standard curves obtained by performing the same sandwich ELISA using already known concentrations of growth hormone. When examining the rates of stimulation for the production of growth hormones in the groups with various doses added, by taking the rate of stimulation for the production of growth hormone for the reference group with no peptides added as 100%, the following was obtained. The results are presented in the Table 4 below.

TABLE 4

| quantity of peptide added (µg/well) | stimulation rate of growth hormone production (%) |
| --- | --- |
| 0 | 100.0 |
| 0.01 | 101.2 |
| 0.1 | 124.1 |
| 1 | 175.6 |
| 10 | 190.4 |

As clearly demonstrated in Table 4, the peptide synthesized in Example 8 have the effect on growth hormone producing cells of stimulating the production of growth hormones. Therefore, the peptides are considered to lead to the stimulation of growth, and therefore useful as a remedy for dwarfism.

What is claimed is:

1. A method for the treatment of a patient having diabetes comprising administering to the patient a therapeutically effective amount of a peptide comprising the sequence of SEQ ID NO:1, wherein said peptide consists of no more than 9 amino acids in length, and wherein said peptide causes increased production of insulin by insulin-producing cells.

2. The method of claim 1 wherein the sequence of said peptide consists of the sequence of SEQ ID NO:1.

3. The method of claim 1 wherein the treatment is administered intravenously, intramuscularly, hypodermically, orally or percutaneously.

4. A method for the treatment of a patient having diabetes comprising administering to the patient a therapeutically effective amount of a peptide comprising the sequence of SEQ ID NO:5, wherein said peptide consists of no more than 9 amino acids in length, and wherein said peptide causes increased production of insulin by insulin-producing cells.

5. The method of claim 4 wherein the sequence of said peptide consists of the sequence of SEQ ID NO:1.

6. The method of claim 4 wherein the treatment is administered intravenously, intramuscularly, hypodermically, orally or percutaneously.

7. In a method of treating diabetes comprising the administration to a patient in need of treatment a therapeutically effective amount of a peptide, the improvement comprising administering to the patient a peptide comprising the sequence of SEQ ID NO:1, wherein said peptide consists of no more than 9 amino acids in length, and wherein said peptide causes increased production of insulin by insulin-producing cells.

8. In a method of treating diabetes comprising the administration to a patient in need of treatment a therapeutically effective amount of a peptide, the improvement comprising administering to the patient a peptide comprising the sequence of SEQ ID NO:5, wherein said peptide consists of no more than 9 amino acids in length, and wherein said peptide causes increased production of insulin by insulin-producing cells.

* * * * *